US012667494B2

(12) United States Patent
Schütz et al.

(10) Patent No.: US 12,667,494 B2
(45) Date of Patent: Jun. 30, 2026

(54) WOUND DRESSING

(71) Applicant: Essity Hygiene and Health Aktiebolag, Gothenburg (SE)

(72) Inventors: Patrick Schütz, Hamburg (DE); Torsten Schramm, Hamburg (DE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 0 days.

(21) Appl. No.: 19/115,413

(22) PCT Filed: Sep. 27, 2022

(86) PCT No.: PCT/EP2022/076879
§ 371 (c)(1),
(2) Date: Mar. 26, 2025

(87) PCT Pub. No.: WO2024/067958
PCT Pub. Date: Apr. 4, 2024

(65) Prior Publication Data
US 2026/0000546 A1      Jan. 1, 2026

(51) Int. Cl.
A61F 13/00       (2024.01)
A61F 13/0203    (2024.01)
A61F 13/0206    (2024.01)

(52) U.S. Cl.
CPC ...... A61F 13/0209 (2013.01); A61F 13/0213 (2013.01)

(58) Field of Classification Search
CPC .......... A61L 15/60; A61L 15/18; A61L 15/42; A61L 15/28; A61L 15/46; A61L 15/24;

A61L 15/22; A61L 15/26; A61L 15/425; A61L 15/20; A61L 2300/404; A61L 15/225; A61L 15/58; A61L 15/48; A61L 15/44; A61L 15/16; A61L 15/50; A61L 15/585; A61L 15/56; A61L 2300/102; A61L 2300/104; A61L 15/62; A61L 15/00; A61L 15/34; A61L 2300/10;
(Continued)

(56) References Cited

U.S. PATENT DOCUMENTS 5,409,771 A      4/1995  Dahmen et al.
10,653,570 B2 *  5/2020  Wirtz ................ A61F 13/53418
(Continued)

FOREIGN PATENT DOCUMENTS

CA        2031435 A1 *  6/1991
EP        0149998 A2    7/1985
(Continued)

OTHER PUBLICATIONS

NO 167760 Translation (Year: 1991).*
(Continued)

*Primary Examiner* — Kim M Lewis
(74) *Attorney, Agent, or Firm* — CANTOR COLBURN LLP

(57)            ABSTRACT

The present invention relates to a wound dressing comprising an absorbent core, the absorbent core comprising a first group of superabsorbent particles characterized in that the superabsorbent particles of the first group are encapsulated in a first water-soluble material. The invention further relates to an absorbent core for such a wound dressing.

24 Claims, 3 Drawing Sheets

(58) Field of Classification Search

CPC ........... A61L 2300/216; A61L 2300/11; A61L 2300/802; A61L 9/014; A61L 2300/606; A61L 2300/202; A61L 2300/30; A61L 2300/62; A61L 9/01; A61L 2300/00; A61L 2420/04; A61L 26/0085; A61L 26/0095; A61L 15/12; A61L 2300/232; A61L 15/38; A61L 2400/12; A61L 2/18; A61L 2/186; A61L 2/22; A61L 2/235; A61L 2202/22; A61L 15/54; A61L 28/0049; A61L 2/16; A61L 2202/21; A61L 2202/24; A61L 2300/108; A61L 2300/428; A61L 2300/622; A61L 2400/10; A61L 2300/21; A61L 2300/214; A61L 2300/602; A61L 15/40; A61L 2300/412; A61L 2300/418; A61L 2300/45; A61L 2/238; A61L 2101/02; A61L 2101/44; A61L 2209/21; A61L 2300/204; A61L 2300/402; A61L 2300/42; A61L 24/001; A61L 2400/06; A61L 26/0061; A61L 27/12; A61L 27/58; A61L 9/015; A61L 9/044; A61L 15/32; A61L 2/232; A61L 2101/48; A61L 2202/20; A61L 2209/22; A61L 2300/114; A61L 2300/208; A61L 2300/22; A61L 2300/252; A61L 2300/254; A61L 2300/406; A61L 2300/414; A61L 2300/434; A61L 2300/442; A61L 2300/60; A61L 24/0015; A61L 24/0026; A61L 24/02; A61L 2400/04; A61L 2420/00; A61L 26/0066; A61L 26/0076; A61F 13/53; A61F 2013/530481; A61F 13/15; A61F 13/535; A61F 13/15203; A61F 2013/530496; A61F 13/15658; A61F 13/534; A61F 2013/530569; A61F 2013/530554; A61F 13/5323; A61F 13/8405; A61F 13/511; A61F 2013/15422; A61F 13/0209; A61F 2013/530583; A61F 2013/00748; A61F 2013/530007; A61F 13/539; A61F 2013/530445; A61F 2013/530671; A61F 13/5376; A61F 2013/15406; A61F 13/533; A61F 2013/15463; A61F 2013/530613; A61F 2013/530788; A61F 2013/00472; A61F 2013/0091; A61F 2013/51078; A61F 2013/00927; A61F 2013/15951; A61F 2013/5104; A61F 2013/530189; A61F 2013/530525; A61F 2013/15544; A61F 2013/530708; A61F 13/531; A61F 2013/5307; A61F 13/15634; A61F 13/537; A61F 2013/53062; A61F 2013/15373; A61F 2013/15967; A61F 2013/530744; A61F 13/53717; A61F 2013/530715; A61F 2013/53782; A61F 13/15699; A61F 2013/530489; A61F 2013/530532; A61F 2013/530686; A61F 13/536; A61F 13/53743; A61F 2013/8408; A61F 13/49; A61F 2013/00731; A61F 13/022; A61F 13/47209; A61F 2013/00251; A61F 2013/00859; A61F 2013/53051; A61F 2013/8426; A61F 13/53752; A61F 13/538; A61F 13/15211; A61F 2013/530729; A61F 13/42; A61F 13/84; A61F 13/01029; A61F 13/513; A61F 13/53704; A61F 13/53708; A61F 2013/530547; A61F 2013/15382; A61F 2013/15512; A61F 2013/530751; A61F 13/532; A61F 2013/530722; A61F 13/0203; A61F 13/15626; A61F 13/49007; A61F 2013/53778; A61F 2013/5395; A61F 13/0276; A61F 13/53747; A61F 2013/530649; A61F 2013/8497; A61F 13/4758; A61F 13/53756; A61F 2013/5349; A61F 13/0206; A61F 13/0223; A61F 13/4702; A61F 2013/53445; A61F 2013/53908; A61F 13/00; A61F 13/472; A61F 2013/1591; A61F 2013/530131; A61F 13/01042; A61F 13/15731; A61F 2013/15357; A61F 2013/530299; A61F 2013/53463; A61F 2013/53472; A61F 13/01046; A61F 13/4755; A61F 13/551; A61F 2013/15016; A61F 2013/530737; A61F 2013/53786; A61F 13/515; A61F 2013/15284; A61F 2013/15943; A61F 2013/49092; A61F 2013/530642; A61F 2013/8435; A61F 2013/8447; A61F 2013/8461; A61F 13/00987; A61F 13/023; A61F 13/15252; A61F 13/53418; A61F 13/53427; A61F 2013/00604; A61F 2013/530562; A61F 2013/530948; A61F 2013/530956; A61F 2013/53925; A61F 13/15707; A61F 13/47218; A61F 13/495; A61F 13/51462; A61F 2013/15365; A61F 2013/51023; A61F 2013/53795; A61F 13/0289; A61F 13/4704; A61F 13/49001; A61F 13/53409; A61F 2013/422; A61F 2013/4568; A61F 2013/530656; A61F 13/00063; A61F 13/0253; A61F 13/15642; A61F 13/49017; A61F 13/49426; A61F 13/51121; A61F 13/51305; A61F 13/58; A61F 2013/00548; A61F 2013/00676; A61F 2013/15146; A61F 2013/1556; A61F 2013/5315; A61F 13/47; A61F 13/49011; A61F 13/49466; A61F 13/512; A61F 13/51394; A61F 2013/00268; A61F 2013/00523; A61F 2013/00663; A61F 2013/00697; A61F 2013/0074; A61F 2013/00744; A61F 2013/00753; A61F 2013/00757; A61F 2013/00782; A61F 2013/00885; A61F 2013/1513; A61F 2013/15243; A61F 2013/49041; A61F 2013/4958; A61F 2013/51452; A61F 2013/53016; A61F 2013/53975; A61F 2013/8488; A61F 13/025; A61F 13/15666; A61F 13/15804; A61F 13/4751; A61F 13/51474; A61F 13/55115; A61F 13/82; A61F 2013/4531; A61F 2013/530759; A61F 2013/530766; A61F 2013/530839; A61F 2013/53734; A61F 2013/53958; A61F 13/01008; A61F 13/01012; A61F 13/01017; A61F 13/01038; A61F 13/02; A61F 13/0279; A61F 13/15577; A61F 13/1565; A61F 13/47263; A61F 13/4753; A61F 13/49015; A61F 13/5116; A61F 13/53713; A61F 2013/51009; A61F 2013/51338; A61F 2013/530153; A61F

2013/530226; A61F 2013/530306; A61F 2013/530832; A61F 2013/530875; A61F 13/0213; A61F 13/0226; A61F 13/141; A61F 13/4756; A61F 13/494; A61F 13/4946; A61F 13/51104; A61F 13/51113; A61F 2013/51033; A61F 2013/51066; A61F 2013/51073; A61F 2013/530051; A61F 2013/530175; A61F 2013/530343; A61F 2013/530678; A61F 2013/530912; A61F 2013/530963; A61F 2013/530978; A61F 2013/53933; A61F 13/00059; A61F 13/01; A61F 13/15617; A61F 13/15747; A61F 13/15772; A61F 13/47227; A61F 13/4902; A61F 13/51464; A61F 13/5511; A61F 13/5514; A61F 13/55145; A61F 2013/00119; A61F 2013/00182; A61F 2013/00319; A61F 2013/00327; A61F 2013/00727; A61F 2013/00825; A61F 2013/00846; A61F 2013/426; A61F 2013/49022; A61F 2013/51139; A61F 2013/51377; A61F 2013/53043; A61F 2013/530518; A61F 2013/530635; A61F 13/00055; A61F 13/01034; A61F 13/0283; A61F 13/05; A61F 13/49009; A61F 13/4942; A61F 13/51; A61F 13/51108; A61F 13/5121; A61F 13/514; A61F 13/55105; A61F 2013/00255; A61F 2013/15292; A61F 2013/15414; A61F 2013/1543; A61F 2013/15447; A61F 2013/15487; A61F 2013/15495; A61F 2013/49076; A61F 2013/5113; A61F 2013/51147; A61F 2013/51178; A61F 2013/51355; A61F 2013/51409; A61F 2013/530204; A61F 2013/53024; A61F 2013/530364; A61F 2013/530861; A61F 2013/53791; A61F 2013/5386; A61F 13/00051; A61F 13/00991; A61F 13/0243; A61F 13/0246; A61F 13/0259; A61F 13/15764; A61F 13/202; A61F 13/206; A61F 13/47245; A61F 13/496; A61F 13/505; A61F 13/5123; A61F 13/51456; A61F 13/53436; A61F 13/5513; A61F 13/55175; A61F 13/5622; A61F 2013/00089; A61F 2013/00165; A61F 2013/00285; A61F 2013/00314; A61F 2013/00323; A61F 2013/15048; A61F 2013/15471; A61F 2013/15821; A61F 2013/15861; A61F 2013/5055; A61F 2013/51019; A61F 2013/51059; A61F 2013/51076; A61F 2013/5109; A61F 2013/51143; A61F 2013/51322; A61F 2013/51429; A61F 2013/5149; A61F 2013/530182; A61F 2013/530335; A61F 2013/53035; A61F 2013/530598; A61F 2013/530693; A61F 2013/530802; A61F 2013/530897; A61F 2013/530985; A61F 2013/53454; A61F 2013/53739; A61F 2013/53916; A61F 2013/53966; A61F 2013/583; A61F 2013/8414; A61F 2013/842; A61F 2013/8423; A61F 2013/8473; A61F 2013/8479; A61F 13/069; A61F 13/15739; A61F 13/20; A61F 13/36; A61F 13/471; A61F 13/474; A61F 13/49058; A61F 13/49061; A61F 13/49413; A61F 13/49473; A61F 13/4963; A61F 13/51311; A61F 13/51476; A61F 13/51484; A61F 13/51496; A61F 13/5512; A61F 13/56; A61F 13/5611; A61F 13/5616; A61F 13/5644; A61F 13/5655; A61F 13/62; A61F 13/622; A61F 15/001; A61F 2/958; A61F 2013/00153; A61F 2013/00217; A61F 2013/00544; A61F 2013/00714; A61F 2013/00863; A61F 2013/15113; A61F 2013/15121; A61F 2013/15235; A61F 2013/1539; A61F 2013/15439; A61F 2013/15479; A61F 2013/15528; A61F 2013/15552; A61F 2013/15829; A61F 2013/425; A61F 2013/427; A61F 2013/428; A61F 2013/4581; A61F 2013/49031; A61F 2013/49044; A61F 2013/49093; A61F 2013/4944; A61F 2013/51026; A61F 2013/5103; A61F 2013/51038; A61F 2013/51117; A61F 2013/51191; A61F 2013/5127; A61F 2013/5128; A61F 2013/51327; A61F 2013/51407; A61F 2013/51411; A61F 2013/5145; A61F 2013/530145; A61F 2013/530218; A61F 2013/530321; A61F 2013/530386; A61F 2013/53054; A61F 2013/530627; A61F 2013/530817; A61F 2013/530824; A61F 2013/530846; A61F 2013/53089; A61F 2013/530941; A61F 2013/5312; A61F 2013/5355; A61F 2013/53721; A61F 2013/5373; A61F 2013/588; A61F 2013/8491; A61F 2250/0067; A61F 7/032

See application file for complete search history.

(56) References Cited

U.S. PATENT DOCUMENTS

| | | | |
|---|---|---|---|
| 2003/0109840 A1 | 6/2003 | Dodge et al. | |
| 2015/0088085 A1* | 3/2015 | Rovaniemi | A61F 13/0209 |
| | | | 604/385.03 |
| 2015/0190543 A1* | 7/2015 | Marshall | A61L 15/24 |
| | | | 424/443 |

FOREIGN PATENT DOCUMENTS

| | | | | | |
|---|---|---|---|---|---|
| EP | 1682195 A1 | | 7/2006 | | |
| EP | 1985270 A2 | | 10/2008 | | |
| GB | 2280115 A | * | 1/1995 | | |
| NO | 167760 B | * | 8/1991 | | A61F 13/534 |
| WO | WO 03/051412 A1 | * | 6/2003 | | |

OTHER PUBLICATIONS

International Preliminary Report on Patentability for International Application No. PCT/EP2022/076879; International Filing Date: Sep. 27, 2022; Date of Mailing: May 21, 2024; 12 pages.
International Search Report & Written Opinion for International Application No. PCT/EP2022/076879; International Filing Date: Sep. 27, 2022; Date of Mailing: May 4, 2023; 12 pages.

* cited by examiner

WOUND DRESSING

CROSS REFERENCE TO RELATED APPLICATIONS

This application is a National Stage Application of PCT/EP2022/076879, filed Sep. 27, 2022, the contents of which are incorporated by reference in their entirety herein.

TECHNICAL FIELD

The present disclosure relates to an absorbent dressing for attachment to a body part and use in the treatment of skin wounds, in particular wounds showing strong exudation.

BACKGROUND

When skin or other tissue is wounded, the wound usually starts emitting exudate. The exudate includes liquid leaking out of blood or lymph vessels and may contain serum, fibrin and leukocytes. Wounds which include areas of strong infection or inflammation can exude high fluid volumes. To manage these volumes, the wounds are often covered with wound dressings which include an absorbent core that can take up substantial amounts of fluid. Thereby, the fluid can be removed from the wound while the wound is kept moist, thus, promoting wound healing.

These absorbent cores can include, for example, superabsorbent particles as described e.g. in EP 1 985 270 A2. Some superabsorbers can bind up to a factor 1000 of their own weight in fluids. Superabsorbent-containing wound dressings are, therefore, particularly effective. However, in taking up the liquid, the superabsorbent particles which are closest to the wound—i.e. the particles on the proximal side of the dressing—are immediately increasing in volume considerably. Thereby, the expanded particles can slow down or even block the flow of wound exudate into regions of the absorbent core which are located more distally. Bulges can form in the absorbent core that can unpleasantly press onto the wound and the uptake of wound exudate is slowed down. In some instances, the absorbent core can leak exudate back into the wound. The resulting wet—not only moist—environment is detrimental for wound healing.

There is, thus, a need in the art for improved absorbent wound dressings which can take up large volumes of exudate in a continuous manner without suffering from the above-described gel blocking effects.

DESCRIPTION

This problem is solved by an absorbent core and wound dressing as described in the appended claims. The absorbent core of the invention makes use of superabsorbent particles which are encapsulated in a water-soluble material. The onset of absorption by these particles is delayed in comparison with superabsorbent particles which are not encapsulated. A more homogenous distribution of wound exudate in the absorbent core can be achieved.

In a first aspect, the present invention, thus, relates to a wound dressing including an absorbent core, the absorbent core including a first group of superabsorbent particles characterized in that the superabsorbent particles of the first group are encapsulated in a first water-soluble material.

In a second, related, aspect, the invention relates to an absorbent core for a wound dressing, wherein the absorbent core includes a first group of superabsorbent particles which are encapsulated in a first water-soluble material.

The wound dressing is a medical dressing able to absorb fluids, such as wound fluids. It is, thus, an absorbent dressing. The wound dressing can be adapted to be used on skin, e.g. human skin, and will, consequently adhere to the skin of the wearer, e.g. to the skin of a patient. The wound dressing of the invention can be a one-piece dressing. This means that it will not be necessary for the medical personnel applying the dressing to assemble the dressing from several components before its application. Instead, all components of the wound dressing described herein form a unit that holds together without the use of further components or supporting tools. Alternatively, the wound dressing can be adapted to allow the exchange of the absorbent core and/or other elements of the dressing. In these embodiments, the wound dressing can, e.g., include a window element in the covering layer that is adapted to be opened and closed. This has the advantage that the absorbent core can be exchanged once it is saturated with wound exudate. Suitable additional layers and components of a wound dressing are described elsewhere herein.

The absorbent core of the present invention includes a first group of superabsorbent particles which are encapsulated in a first water-soluble material. In addition to this first group of superabsorbent particles, the absorbent core can include additional groups of superabsorbent particles with different properties. These will be described in more detail elsewhere herein.

The superabsorbent particles within the absorbent core enable the core to take up and retain fluids, such as wound fluids (exudate). The terms "wound fluids" or "exudate" refer to fluids which have escaped from a wound, in particular because of inflammatory processes of the blood plasma. The wound fluids or exudates serve to supply the wound bed and the healing processes which are taking place there with a wide array of components, including nutrients for fibroblasts and epithelial cells, growth factors and cytokines. The wound fluids also assist in the cleaning of the wound and the degradation of damaged tissue.

The absorbent core is a flat layer that usually includes a carrier material, such as a woven or non-woven fabric, to stabilise the superabsorbent particles structurally and/or functionally support the superabsorbent particles included in the core.

The superabsorbent particles used in the context of the invention include or consist of superabsorbent material. The superabsorbent material in the particles swells on exposure to water or other liquids such as wound exudate and forms a hydrated gel (hydrogel) by absorbing large amounts of water. Superabsorbent materials are defined herein as materials that exhibit the ability to absorb large quantities of liquid, for example 10 or more parts of liquid per part of superabsorbent material (weight per weight), 20 or more, 30 or more, 40 or more, 50 or more, 60 or more, 70 or more, 80 or more, or 100 or more. In other words, the superabsorbent materials can be materials that can absorb, for example from 10 to 1000 parts of liquid per part of superabsorbent material (weight per weight), from 15 to 1000 parts, or from 50 to 1000 parts. The superabsorbent materials have, in other words, the ability to absorb 10 g/g or more, preferably 15 g/g or more, more preferably 50 g/g, of water (and water-based fluids), when e.g. measured under a confining pressure of 0.3 psi.

The superabsorbent material can be any superabsorbent material suitable for use in the field of wound dressings, in particular a superabsorbent polymer. For example, the superabsorbent material can be a superabsorbent polymer. The superabsorbent material can e. g. be selected from the group consisting of starch graft copolymers, cross-linked carboxymethylcellulose synthetic or natural derivatives, (modified) hydrophilic polyacrylates, cross-linked polyacrylates, cross-linked polyethylenoxides, modified "natural based" materials, such as starch-based superabsorbent materials, or cellulose-based superabsorbent materials. Preferably, the superabsorbent material used in the dressing of the present invention is composed of particles of cross-linked polyacrylates, such as polyacrylic-acid and the salts thereof. The term "modified" can refer to various types of modifications, such as e.g. cross-linking.

Suitable superabsorbent materials are known in the art and are available commercially. For example, starch graft polyacrylate hydrogel powders are available from Hoechst-Celanese (Portsmouth, VA). Other crosslinked sodium polyacrylate superabsorbent particles are marketed under the trademark FAVOR (Degussa AG, Germany).

In line with the standard meaning of the term "particle", the superabsorbent material used in the context of the invention has particulate form. Each superabsorbent particle has a defined volume and mass. It can have a substantially round, rectangular or irregular form and will usually include more than one superabsorbent molecule. The form of the particle is chosen to have a large surface area in relation to its overall volume, e.g. a substantially spherical form. The superabsorbent material within each particle can e.g. be in the form of a granulate, flakes, powder, or fibers. Preferably, the particles are insoluble in the wound exudate.

The mean diameter of the superabsorbent particles is typically within the range of 10 to 950 μm when dry, such as from 100 to 900 μm. It is preferred that the superabsorbent particles have a narrow size distribution, such as a maximal difference in diameter of 700 μm or less, or 500 μm or less.

The superabsorbent particles may be enmeshed or freely disposed in pores or free spaces of the carrier material. Alternatively, the superabsorbent material may be homogenously distributed in the carrier material and attached to it. For example, the carrier material can include hydrophilic polyurethane foam into which superabsorbent particles are mixed prior to foaming, so as to obtain a foam material with the superabsorber material homogenously distributed therein and substantially anchored to the foam. Alternatively, superabsorbent particles can be pressed together and enclosed in a tissue-sheath, e.g. a sheath composed of two fused layers of non-woven material. As a further alternative, superabsorbent particles and fibers can be mixed, e.g. blowmixed. That way, the superabsorbent particles and the fibers can form an absorbent pad with sufficient structural integrity.

The absorbent core may include different groups of superabsorbent particles. One or more of the aforementioned properties can apply to all groups, but each group has distinctive properties. The superabsorbent particles of one group (e.g. the first group) are, hence, distinguishable from the superabsorbent particles from other groups (e.g. the second group). For example, the superabsorbent particles of the first group can be encapsulated in a water-soluble material while the superabsorbent particles of the second group are not encapsulated by a water-soluble material. In another embodiment, the superabsorbent particles of the first group are encapsulated in a first water-soluble material and the superabsorbent particles of the second group are encapsulated in a second water-soluble material which differs from the first water-soluble material. Each superabsorbent particle can, thus, be easily assigned to the correct group if necessary.

The superabsorbent particles, in particular the superabsorbent particles of the first group, can be encapsulated with the water-soluble material in different ways. In a preferred embodiment, the absorbent core includes microcapsules having a core and a shell, wherein the core includes a superabsorbent particle of the first group and the shell includes the first water-soluble material. Alternatively, the absorbent core can include a layer of the first water-soluble material in which the first group of superabsorbent particles is embedded.

In both cases, the water-soluble material covers the respective superabsorbent particles on their entire surface when the absorbent core is dry. Thereby, the water-soluble material initially prevents a premature swelling of the superabsorbent particles. Over time, when exposed to wound exudate, the water-soluble material dissolves and allows the liquid, e.g. the wound exudate, access to the superabsorbent material in the superabsorbent particle. The water-soluble material is, thus, dissolvable by water-based liquids, such as wound exudate.

The water-soluble materials mentioned herein, i.e. the first water-soluble material and the second water-soluble material, can be any suitable water-soluble material known in the art. The water-soluble material can include or consist of a water-soluble polymer material, such as a water-soluble polymer. The water-soluble material can e.g. be selected from the group consisting of polyvinyl alcohol, polyvinylpyrrolidones, polyoxazolines, starch and starch derivatives, polyureas, polyurethanes, polyethers, polyamides, polyesters, polycarbonates, protein such as casein, gelatin, vegetable protein such as soy or corn proteins, modified polysaccharides such as pullulan, pectin, alginate, laminarin and xanthan, hydroxyalkyl celluloses such as hydroxypropyl cellulose and hydroxypropylmethyl cellulose, nonionic surfactants with a polyethylene residue, salts, such as sodium chloride and water-soluble combinations and water-soluble derivatives thereof. In certain preferred embodiments, the water-soluble material is polyvinyl alcohol or a watersoluble derivative thereof. Suitable water-soluble materials are described e.g. in DE 4131939 A1, DE 699 18 879 T2 and U.S. Pat. No. 7,579,402 B2.

In cases in which the water-soluble material forms a layer in which the first group of superabsorbent particles is embedded, the layer will usually have a sheet-like shape. It will, in other words, be flat in a proximal-distal direction and be longer and broader in a plane that is parallel to the proximal and distal surfaces of the absorbent core. A multitude of superabsorbent particles, e.g. all particles of one group, will be embedded in the same layer. The layer can consist of water-soluble material and superabsorbent particles. It can have substantially the same dimensions as the absorbent core in a plane that is parallel to the proximal and distal surfaces of the absorbent core.

The words "proximal" and "distal" are used herein to refer to the position of the respective surface in relation to the wearer when the wound dressing or absorbent core is in use on the wound of a patient. In line with the standard meaning of the terms in the art, "distal" refers to the surface which is farther away from the wearer and "proximal" refers to the surface which is closer to the wearer, i.e. closer to the wound, skin and/or other body surface.

As outlined above, the superabsorbent particles can, alternatively, form the core of a microcapsule. The microcapsule will then include or consist of a core and a shell, wherein the core includes a superabsorbent particle of the first group and the shell includes the first water-soluble material. The core can consist of a superabsorbent particle. The shell can consist of the water-soluble material.

A "microcapsule" as used herein is a small particle, e.g. with the form of a sphere, that encapsulates a core of superabsorbent material in a shell (or wall). The microcapsule will generally have a mean diameter of not more than $1000\,\mu m$, such as from $20\,\mu m$ to $1000\,\mu m$, or preferably from $100\,\mu m$ to $1000\,\mu m$. It is preferred that the microcapsules have a narrow size distribution, such as a maximal difference in diameter of $700\,\mu m$ or less, or $500\,\mu m$ or less.

The water-soluble material is applied to the core such that the resulting shell is preferably thin, e.g. having an average calculated thickness in the dry state of more than $0.1\,\mu m$; preferably the coating layer has an average thickness, from $1\,\mu m$ to $100\,\mu m$, preferably from $1\,\mu m$ to $50\,\mu m$, more preferably from $1\,\mu m$ to $20\,\mu m$, or even from $2$ to $20\,\mu m$ or even from $2$ to $10\,\mu m$. The shell is preferably virtually uniform in thickness and/or shape.

As the potential gel blocking effect occurs mostly in the proximal region of an absorbent core because that region is closest to the wound and, therewith, to the wound exudate, the concentration of microcapsules (containing encapsulated superabsorbent material) can be particularly high at the proximal side of the absorbent core. The concentration of the microcapsules in the most proximal 10 vol.-% of the absorbent core can be, e.g., from $0.1$ to $1500$ g/m$^2$, preferably from $50$ to $1500$ g/m$^2$ and most preferably from $100$ to $1000$ g/m$^2$. This concentration of microcapsules can continue throughout the thickness of the absorbent core, i.e. from the proximal to the distal surface of the absorbent core. Alternatively, the concentration can drop in the more distal portions of the absorbent core. In that case, it is advantageous to have a second group of superabsorbent particles which have a higher concentration in these more distal portions than in a proximal portion.

The aforementioned concentrations of microcapsules can apply to, preferably, the most proximal, 10 vol.-% or more, 15 vol.-% or more, 20 vol.-% or more, 25 vol.-% or more, 30 vol.-% or more, 35 vol.-% or more, 40 vol.-% or more, 45 vol.-% or more, 50 vol.-% or more, 55 vol.-% or more, 60 vol.-% or more, 65 vol.-% or more, 70 vol.-% or more, 75 vol.-% or more, 80 vol.-% or more, 85 vol.-% or more, 90 vol.-% or more, or 95 vol.-% or more, of the absorbent core.

In addition to the aforementioned materials, the absorbent core can include one or more carrier materials. For example, the absorbent core can include a carrier material selected from the group consisting of polyester, cellulose, polyurethan, polyethylene, polypropylene and combinations and derivatives thereof. Polyester and cellulose are particularly preferred carrier materials.

The carrier materials can be formed into a structure that supports the superabsorbent particles in different ways. The absorbent core can, accordingly, include a carrier material selected from the group consisting of non-woven, woven, warp-knitted, and weft-knitted material.

Non-woven materials are fabric-like materials made from short and/or long fibres bonded together by chemical, mechanical, heat or solvent treatment. The non-woven can e.g. be manufactured by milling the fibres. Examplary non-woven materials include airlaids, laminates, or composite material. Airlaid fabrics are e.g. non-woven materials made of cellulose and polyolefin fibers. In one embodiment, the carrier material is an airlaid mat containing a cellulose nonwoven.

The absorbent core can be relatively thick. The core can, e.g., have a thickness of 1 mm or more, preferably 2 mm or more, when it is dry. In other words, the thickness of the absorbent core can be from 1 mm to 10 mm, such as from 2 mm to 5 mm. The thickness of the absorbent core can increase considerably during fluid uptake, e.g., up to 5 cm or more. In other words, the thickness of the absorbent core can increase 10-fold or more during fluid uptake.

The absorbent core can have a rectangular (such as square) shape, e.g., a rectangular shape with rounded edges; an oval shape; a round shape or an irregular shape. The term "shape" as mentioned herein, refers to the shape that can be seen when looking at the absorbent core or other part of the wound dressing described herein from proximal or distal direction, i.e., the shape in an XY-plane, wherein the XY-plane is substantially parallel to the skin or surface of the body part on which the wound dressing can be worn, i.e., substantially parallel to the adhesive layer.

Usually, the shape of the absorbent core will be substantially identical to that of the wound dressing. For example, a rectangular wound dressing can include a rectangular absorbent core; an oval wound dressing can include an oval absorbent core. It will be understood that the core will be smaller than the wound dressing in XY-plane, i.e., smaller than the covering layer and the wound-contact layer.

The absorbent core may have a length and width of, e.g., from 1 cm to 35 cm, preferably from 2 cm to 30 cm, more preferably 3 to 20 cm. For example, an absorbent core can have a square shape with a width and length of from 3 to 5 cm, such as 4 cm. In particular embodiments, the absorbent core can have a square shape with a width and length of from 2 to 6 cm, the sheath layers and the adhesive sheath layer can have a square shape with a width and length of from 6 to 10 cm.

The absorbent core has distal and proximal surfaces. The distal surface of the absorbent core can be adjacent to a distal covering layer. The proximal surface of the absorbent core can be adjacent to the wound contact layer. Usually, the absorbent core will not be attached to the adjacent layers so that it is relatively free to move inside the sheath and not restricted in its expansion during the uptake of wound fluids.

The absorbent core can include a second group of superabsorbent particles which are not encapsulated by a water-soluble material. This second group of superabsorbent particles can, hence, be in direct contact with the carrier material when the absorbent core is dry. As a result, the second group of superabsorbent particles will be the first ones to take up liquid once it is in contact with a source of liquid, e.g., wound exudate. The second group of superabsorbers can be distributed in the absorbent core similarly to the first group. In these cases, the encapsulation of the first group will simply serve to delay the onset of absorption by those particles. Alternatively, the second group of superabsorbers can be distributed in the absorbent core in a manner that differs from the distribution of the first group of superabsorbers, for example in an opposite (inverse) manner. For example, while the first group of superabsorbent particles can be present in a concentration gradient that has its highest concentration on the proximal side of the absorbent core, the second group of superabsorbent particles can be present in a concentration gradient that has its highest concentration on the distal side of the absorbent core.

The absorbent core can additionally or alternatively include a third group of superabsorbent particles which are encapsulated in a second water-soluble material. The encapsulation of the third group of superabsorbent particles can be analogous to the encapsulation of the first group of superabsorbent particles described herein. However, the second water-soluble material will differ from the first water-soluble material, for example in the time it takes to dissolve. For this purpose, the second water-soluble material can have a different chemical structure or a different thickness.

The absorbent core can include the third group of superabsorbent particles in the form of microcapsules having a core and a shell, wherein the core includes a superabsorbent particle of the third group and the shell includes the second water-soluble material. The second water-soluble material can have a faster dissociation rate, i.e. dissolve faster, than the first water-soluble material. Suitable pairs of first and second water-soluble materials can be determined by a person skilled in the art. For example, the first water-soluble material can consist of polyvinyl alcohol (PVA) or modified polyvinyl alcohol and the second water-soluble material can consist of another modified polyvinyl alcohol. The dissociation rate of the PVA can be modulated by modifying the extent of crosslinking, modifying the length of the polymer chain, introducing different types of modification and modulating the hydrophilicity.

As noted above, the different groups of superabsorbent particles can be arranged in the absorbent core in an inverse (opposite) manner that efficiently prevents gel blocking. For example, the absorbent core can have a proximal surface and a distal surface and the majority of the superabsorbent particles of the first group are closer to the proximal surface than to the distal surface. It has been shown to be efficient, when from 55% by weight to 100% by weight of the superabsorbent particles of the first group are closer to the proximal surface than to the distal surface, e.g. from 60 to 100% by weight, from 65 to 100% by weight, from 65 to 100% by weight, from 70 to 100% by weight, from 75 to 100% by weight, from 80 to 100% by weight, from 85 to 100% by weight, or from 90 to 100% by weight.

The majority of the (unencapsulated) superabsorbent particles of the second group can be closer to the distal surface than to the proximal surface. It has been shown to be efficient, when from 55% by weight to 100% by weight of the superabsorbent particles of the second group are closer to the distal surface than to the proximal surface, e.g. from 60 to 100% by weight, from 65 to 100% by weight, from 65 to 100% by weight, from 70 to 100% by weight, from 75 to 100% by weight, from 80 to 100% by weight, from 85 to 100% by weight, or from 90 to 100% by weight.

In case the absorbent core includes a third group of superabsorbent particles which are encapsulated in a second water-soluble material, the majority of this group of superabsorbent particles can be in the middle of the absorbent core, between the proximal and the distal surface.

To achieve this distribution, the superabsorbent particles of the first group can form a substantially continuous negative concentration gradient through at least a portion of the thickness of the absorbent core between the proximal surface and the distal surface, e.g. through to the entire thickness of the absorbent core. Methods for producing such gradients are known in the art and include, e.g., successively spreading different amounts of superabsorbent particles during production of the superabsorbent core. "Negative concentration gradient between proximal surface and distal surface" means that the concentration decreases from proximal to distal, i.e. the concentration is highest near the proximal surface.

The second group of superabsorbent particles can form a substantially continuous positive concentration gradient through at least a portion of the thickness of the absorbent core between the proximal surface and the distal surface, such as through the entire thickness of the absorbent core. "Positive concentration gradient between proximal surface and distal surface" means that the concentration increases from proximal to distal, i.e., the concentration is highest near the distal surface.

The third group of superabsorbent particles can form a substantially continuous positive concentration gradient through at least a portion of the proximal half of the absorbent core between the proximal surface and middle (between proximal and distal surfaces) and/or a substantially continuous negative concentration gradient through at least a portion of the distal half of the absorbent core between the middle (between proximal and distal surfaces) and the distal surface. This means that the concentration increases from proximal to the middle and then decreases from the middle to the distal surface.

Alternatively, the absorbent core can include different, distinct layers, wherein the different groups of superabsorbent particles are included in different layers. For example, the absorbent core can include a proximal layer and a distal layer and the first group of superabsorbent particles is included in the proximal layer. The second group of superabsorbent particles can be included in the distal layer. The distal layer can be free of encapsulated superabsorber particles.

The distal layer can be adjacent to the proximal layer. Alternatively, the absorbent core can additionally include a middle layer that includes the third group of superabsorbent particles.

When the superabsorbent particles of the first group form the core of microcapsules, the concentration of microcapsules in the proximal layer can be from 0.1 to 1500 $g/m^2$, preferably from 0.1 to 1250 $g/m^2$ and most preferably from 0.1 to 1000 $g/m^2$, e.g., from 10 to 1000 $g/m^2$.

To enhance the uptake of the wound exudate into the absorbent core, the absorbent core can include channels. These channels are adapted for the passage of wound exudate. The channels can, e.g., be included in the proximal layer. Usually, the channels will be free of material. They can be established in the absorbent core by introducing pores or perforations into a layer, e.g., the proximal layer. Suitable mechanical processes for introducing such perforations are known in the art. One exemplary process involves mechanically stamping perforations into the absorbent core.

The carrier material in the different layers of the absorbent core can be adapted, so that the wound exudate is more quickly transported through the proximal layer and into the distal layer. The carrier material of the distal layer may, e.g., have a higher absorption capacity and/or the carrier material of the proximal layer can have better wicking properties. In particular embodiments, the proximal layer includes a polyester-based carrier material. In addition or alternatively, the distal layer can include a cellulose-based carrier material.

It will be understood that the wound dressing of the invention can additionally include further layers with various properties—such as layers which promote adherence to the skin or enhance the integrity of the dressing and/or layers which have additional functions, such as layer which are suitable to enhance the wound healing process by providing additional absorption capacity or releasing active agents which support the wound healing process.

The wound dressing can, for example include or consist of (a) a covering layer; (b) the absorbent core on the wound facing side of the covering layer, and (c) a wound-contact layer on the wound facing side of the absorbent core. The absorbent core can, further, be located between a distal and a proximal sheath layer. The wound dressing can, moreover, include an adhesive layer on the wound facing side of the wound-contact layer.

The covering layer is usually located on the distal side of the absorbent core and other layers and, thus, farthest away from the wound and skin surface when the wound dressing is worn. In some embodiments the covering layer has no direct contact to the surface of the skin of the wearer, because the wound contact layer can have essentially the same size and shape as the covering layer and can be located between the covering layer and the surface of the skin or other body part to be treated over the entire area of the covering layer. There is, thus, no need to coat the covering layer with an adhesive to stick to the skin or other body part to be treated. The covering layer can be entirely free of adhesives. The cohesion between the covering layer and the other layers of the dressing can be ensured by an adhesive layer.

The covering layer can be highly flexible to allow for an increase in volume of the absorbent core. The covering layer can be stretched and, for this purpose, includes a stretchable material. The material can be elastically and/or plastically stretchable. The covering layer may have a tensile strength of from 15 to 30 N/25 mm. It can have an elongation of from 400% or more, preferably 500% or more.

The covering layer can be liquid-impermeable, specifically water-impermeable. At the same time, it can be vapor permeable. This ensures that no wound fluid leaks to the outside of the dressing, but that the dressing has a good breathability.

Suitable materials which have the aforementioned properties are known in the art. The covering layer may, for example, consist of or include a material selected from the group consisting of polyurethane and co-polyester, wherein a polyurethane is preferred. The polyurethane may be a thermoplastic polyurethane or a non-thermoplastic polyurethane.

The thickness of the covering layer ensures the desired flexibility as well as the desired stability of the covering layer. The layer can have a weight of from 15 to 35 g/m², preferably 20 to 30 g/m².

The wound dressing according to the invention can further include a wound-contact layer on the wound-facing side of the absorbent core. The wound contact layer can include an opening, through which fluid can pass from the wound into the absorbent core. Usually, the opening will be substantially in the centre of the wound contact layer resulting in a frame shape or frame-like shape of the wound contact layer. The wound contact layer may be liquid-impermeable. In alternative embodiments, the wound contact layer is liquid-permeable. In these embodiments, the wound contact layer does not need to have a large opening to let the wound exudate pass.

The wound contact layer can have a wound-facing proximal side. On this side, an adhesive layer can be on the wound contact layer. The adhesive layer is adapted to reversibly attach the wound dressing to the skin of a wearer. The wound contact layer, further, has a distal side adhering to an outer rim of the covering layer or to the outer rim of other layers disposed between the covering layer and the wound contact layer.

The adhesive layer can include a first adhesive. The first adhesive is adapted to adhere to the surface of a body part, preferably the skin, of a wearer. It furthermore ensures that the dressing can be removed from the skin substantially without harming the surface of the body part. It has been discovered that a particularly suitable first adhesive is an adhesive which includes a silicone.

To ensure a firm attachment of the dressing to the skin of the wearer—also during expansion of the absorbent core—

10 the first adhesive has preferably a high adhesion to steel value, such as from 0.5 N/cm to 0.8 N/cm, preferably from 0.6 to 0.7 N/cm.

The absorbent core can be located between a distal and a proximal sheath layer. These layers can form a sheath fully enclosing the absorbent core. The sheath may be closed by sealing the outer edges of the proximal and distal sheath layers.

The sheath, hence, includes a proximal sheath layer on the proximal side of the absorbent core and a distal sheath layer on the distal side of the absorbent core. The sheath may consist of the aforementioned layers. It is, nevertheless, also possible to add further layers to the sheath, for example to increase the absorptive capacity and/or the structural integrity of the sheath.

The proximal sheath layer and the distal sheath layer in the wound dressing may be sealed together along a sealed edge. The sealed edge may run around the entire circumference of the sheath in a plane that is substantially parallel to the wound contact layer. The sealed edge can have a width of from 0.5 cm to 3 cm, from 0.8 cm to 2.5 cm, preferably from 1 cm to 1.8 cm. In other words, the sealed edge can have a width of 0.5 cm or more, 0.75 cm or more, 1 cm or more. The width of the sealed edge can be the same around the entire circumference of the sheath.

The sheath layers may have a length and width of, e.g., from 2 cm to 40 cm, from 3 cm to 30 cm, preferably from 4 to 25 cm, more preferably from 6 cm to 10 cm. For example, the sheath layers can have a substantially square shape with a width and length of about 9 to 11 cm.

The sheath layers, in particular the proximal sheath layer are liquid-permeable layers. The material of the sheath layers will support the fluid uptake by the absorbent core, e.g., by slowing the uptake of fluid, increasing the speed of uptake or even adding further absorptive capacity. Preferably, the sheath layers increase the speed of fluid uptake from the wound to the absorbent core, e.g., by making use of capillary forces in the sheath layers or the like. The sheath layers will usually have good wicking properties.

Certain absorbent materials are known to develop adherence to the wound bed. This adherence is considered detrimental, since it usually leads to pain and damage of the newly formed wound tissue during dressing removal, thereby delaying healing. The material of the proximal and, optionally, also the distal sheath layer may therefore be a low-adherent material, preferably selected from the group of low-adherent materials consisting of polymer films or fabrics (woven or non-woven), usually treated in a way to render them less adherent to the wound. Commercial products including non-adherent or low-adherent layers are, e.g., Profore™ WCL (sold by Smith&Nephew), Mepitel® (sold by Mölnlycke Health Care). The term "low-adherent" material is herein used to describe materials which have a lower adherence to a wound bed than the absorbent core.

The proximal sheath layer and/or the distal sheath layer may, e.g., include or consist of a woven or non-woven material, wherein the latter is preferred. The non-woven can e.g. consist of or include of a material selected from the group consisting of polypropylene, polyester, co-polyester and combinations thereof. The non-woven material can be spun-bound. The material can have a filament-laid structure.

In order to allow the absorbent core to expand within the sheath, the outer dimensions of the unwetted absorbent core are smaller than the inner dimensions of the sheath.

The sheath encloses an inner sheath space that has an inner sheath area extending parallel to the wound contact layer within the flat-lying and unwetted wound dressing. The inner sheath space is the volume of the room inside the sheath when no absorbent core would be present within the space and the layers of the wound dressing are not elastically or plastically deformed. The inner sheath space is, thus, limited on the proximal side by the proximal sheath layer, on the distal side by the distal sheath layer and laterally by the sealed outer edge.

The inner sheath area is one cross-section of the inner sheath space at its maximal expansion. Usually, the inner sheath area is substantially identical to the area of the part of the sheath layers which is not partaking in the sealed outer edge. The inner sheath area can have a size of from 2 $cm^2$ to 1500 $cm^2$, from 4 $cm^2$ to 840 $cm^2$, from 9 $cm^2$ to 570 $cm^2$, or from 15 $cm^2$ to 80 $cm^2$, such as 25 $cm^2$.

The absorbent core has an outer area extending parallel to the wound contact layer within the flat-lying and unwetted wound dressing. The outer area is the surface area of maximal expansion of the absorbent core in a plane that is substantially parallel to the wound contact layer. This outer area of the absorbent core can have a size of from 1 $cm^2$ to 1225 $cm^2$, preferably from 4 $cm^2$ to 900 $cm^2$, more preferably 9 $cm^2$ to 36 $cm^2$, such as 16 $cm^2$. In exemplary embodiments, the outer area of the absorbent core may, thus, be from 1 $cm^2$ to 1225 $cm^2$ and the inner sheath area from 2 $cm^2$ to 1500 $cm^2$.

It can be seen that the size of the outer area of the absorbent core is smaller than the size of the inner sheath area. The outer area of the absorbent core can, e.g., be from 40% to 90% of the size of the inner sheath area (wherein the size of the inner sheath area is 100%), 45% to 85%, 50% to 80%, 55% to 75%, 60% to 70%, such as about 65%. In other words, the size of the outer area of the absorbent core is preferably 90% or less of the size of the inner sheath area, 85% or less, 80% or less, 75% or less, 70% or less, 65% or less, wherein 75% or less is particularly preferred. All of the values mentioned herein refer to the wound dressing in an unwetted state if not specifically indicated otherwise.

BRIEF DESCRIPTION OF FIGURES

Exemplary embodiments of the invention are shown schematically in the drawings.

These and other aspects of the invention will be apparent from and elucidated with reference to the embodiments described hereinafter.

DESCRIPTION OF EMBODIMENTS

Additional advantages, characteristics, and features of the present invention will become clear from the following detailed description of exemplary embodiments with reference to the attached drawings. However, the invention is not restricted to these exemplary embodiments.

Figure 1:
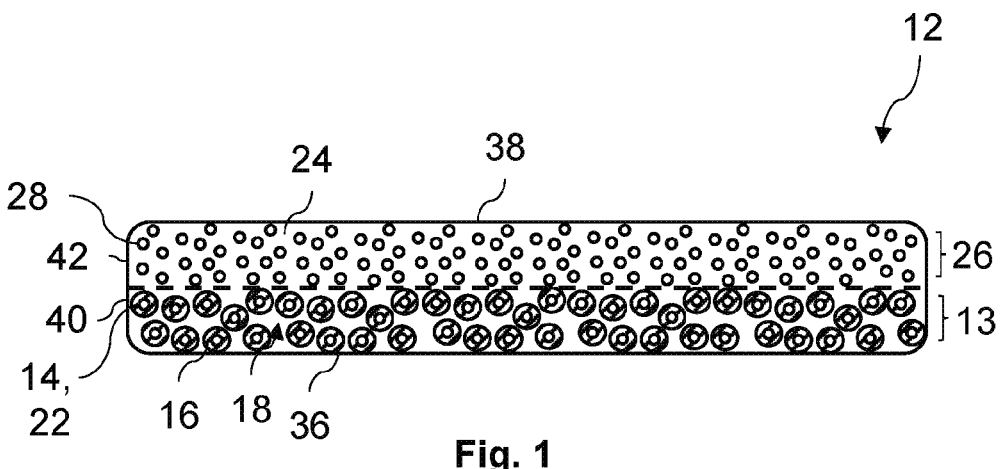
FIG. 1 schematically shows an absorbent core according to the present invention, which includes two layers with different groups of superabsorbent particles, wherein the proximal layer includes a first group of encapsulated superabsorbent particles and the distal layer includes a second group of superabsorbent particles which are not encapsulated.

FIGS. 1 to 4 schematically show different embodiments of absorbent cores 12 according to the present invention. FIG. 1 shows an absorbent core 12 which includes two distinct layers 40, 42 with different groups of superabsorbent particles 14, 28. A proximal layer 40 which is designed to be closest to the patient's wound when the absorbent core 12 is in use, includes a first group 13 of encapsulated superabsorbent particles 14. The superabsorbent particles 14 are encapsulated in a roughly spherical, water-soluble shell 22 of water-soluble material 16, thus, forming microcapsules 18. The distal layer 42 includes a second group 26 of superabsorbent particles 28 which are not encapsulated.

When the absorbent core 12 is in use, then the proximal surface 36 of the absorbent core 12 will face towards the wound and/or skin, while its distal surface 38 will face away from the wound and/or skin. The wound exudate will be taken up through the proximal surface 36 into the absorbent core, thus, passing the first group 13 of superabsorbent particles 14 first before reaching the second group 26 of superabsorbent particles 28. The water-soluble material 16 around the superabsorbent particles 14 of the first group 13 will have to dissolve before these superabsorbent particles 14 can start to take up liquid and swell. In the meantime, the wound exudate can freely pass through the proximal layer 40 and reach the superabsorbent particles 28 of the second group 26. Thereby, any potential clogging caused by swelling in the proximal layer 40 is reduced to a minimum.

Figure 2:
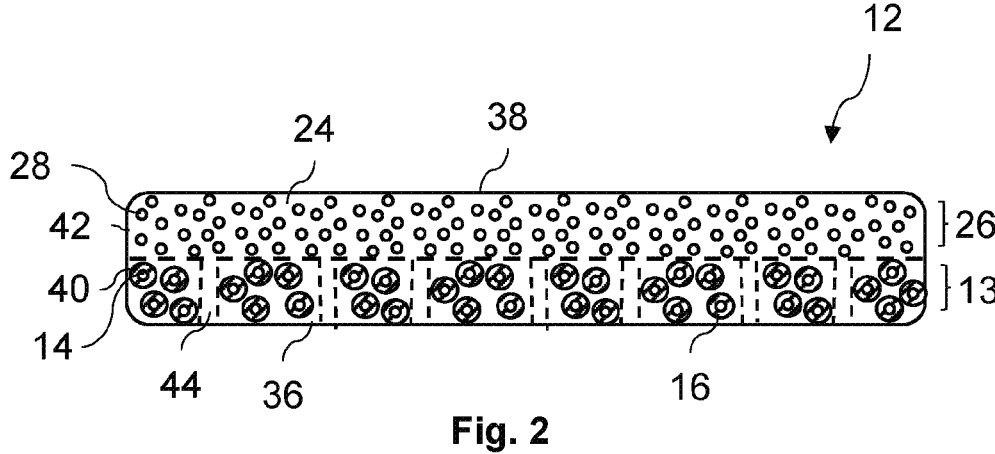
FIG. 2 schematically shows an alternative absorbent core according to the present invention, which includes two layers with different groups of superabsorbent particles, wherein the proximal layer includes a first group of encapsulated superabsorbent particles and the distal layer includes a second group of superabsorbent particles which are not encapsulated, and wherein the proximal layer includes channels for the uptake of wound exudate.

The absorbent core 12 shown in FIG. 2 differs from the absorbent core 12 in FIG. 1 in that the proximal layer 40 additionally includes channels 44 which further accelerate the transport of liquid through the proximal layer 40 into the distal layer 42. The channels 44 are introduced by mechanically introducing perforations into the proximal layer 40 before the proximal layer 40 and the distal layer 42 are combined to form the absorbent core 12.

Figure 3:
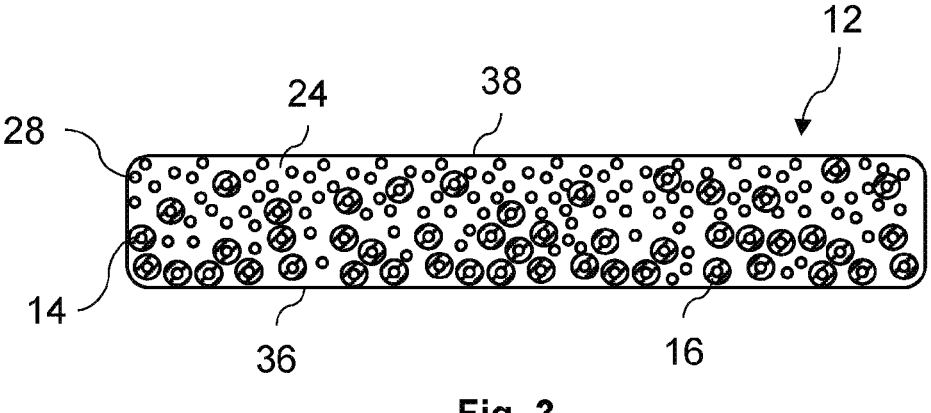
FIG. 3 schematically shows another alternative absorbent core according to the present invention, which includes two different groups of superabsorbent particles which are distributed in a positive and a negative concentration gradient throughout the absorbent core, respectively.

FIG. 3 shows another alternative absorbent core, which differs from those in FIGS. 1 and 2 in that it does not include distinct distal and proximal layers. Instead, the first group 13 of superabsorbent particles 14 and the second group 26 of superabsorbent particles 28 are mixed within the same layer of the absorbent core. The groups are mixed in a manner that ensures a higher concentration of the encapsulated superabsorbent particles 14 near the proximal surface 36 than near the distal surface 38. In other words, the super absorbent particles 28 which are encapsulated in a water-soluble material 16 are distributed in a negative concentration gradient throughout the absorbent core 12 (when assessed from proximal to distal side). In contrast the superabsorbent particles 28, which are not encapsulated, are distributed in a positive concentration gradient throughout the absorbent core 12 (when assessed from proximal to distal side). In other words, the superabsorbent particles 28, which are not encapsulated, have a higher concentration near the distal surface 38 than near the proximal surface 36.

Figure 4:
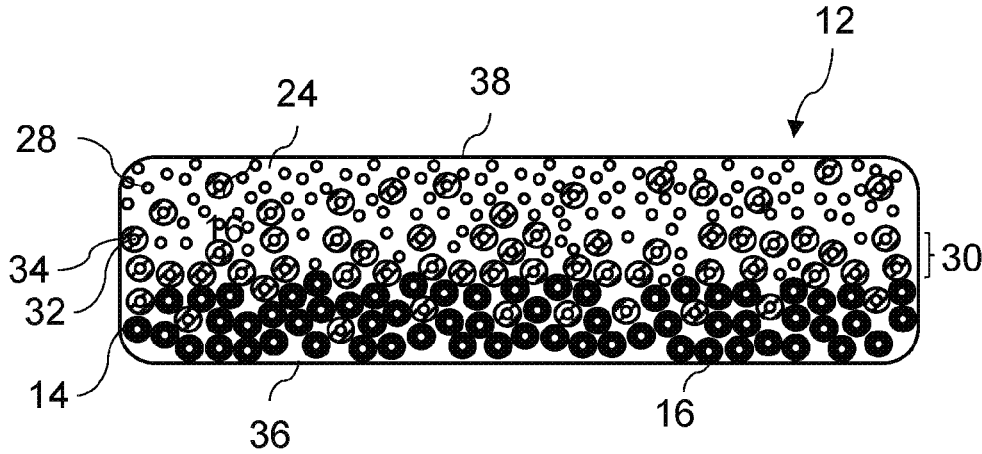
FIG. 4 schematically shows another alternative absorbent core according to the present invention, which includes three different groups of superabsorbent particles which are distributed in different concentration gradients throughout the absorbent core.

FIG. 4 equally shows an absorbent core 12, which does not include distinct layers with superabsorbent particles. The absorbent core 12 of this embodiment includes three inter-mixed groups 13, 26, 30 of superabsorbent particles 14, 28, 32. Each group 13, 26, 30 is distributed in the absorbent core 12 in a gradient that differs from the gradient of the other two groups. Specifically, in addition to the two groups 13, 26 described above for the embodiment of FIG. 3, the embodiment of FIG. 4 includes a third group 30 of superabsorbent particles 32 which has its highest concentration in the middle region of the absorbent core 12, i.e. the middle region between the proximal surface 36 and the distal surface 38. The superabsorbent particles 32 of the third group 30 have lower concentrations towards the proximal surface 36 as well as the distal surface 38. They are encapsulated in a second-water soluble material 34 that has a faster dissociation rate than the first water-soluble material 16. Accordingly, the superabsorbent particles 32 of the third group 30 will sooner start to take up wound exudate than the superabsorbent particles 14 of the first group 13 because their water-soluble shell dissolves faster.

Figure 5:
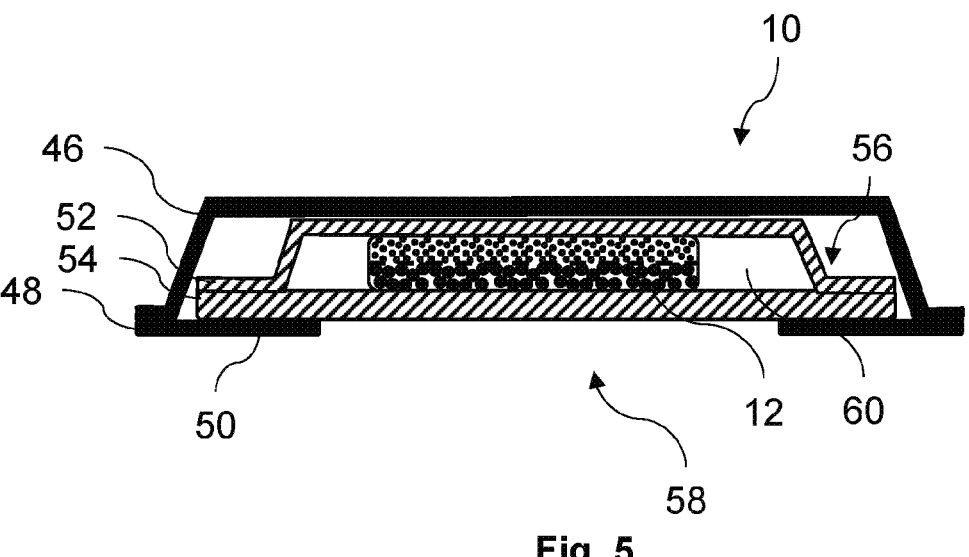
FIG. 5 schematically shows a cross section of a wound dressing according to the present invention, including the absorbent core shown in FIG. 1.
Figure 6:
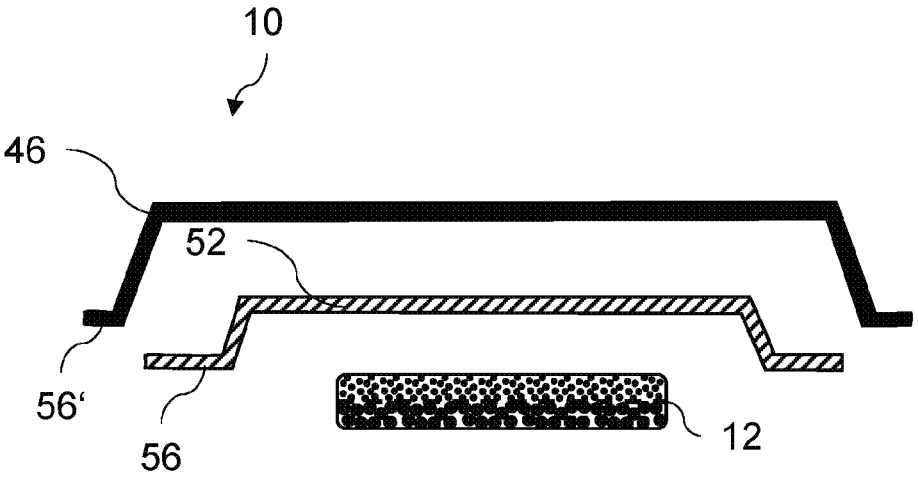
FIG. 6 schematically shows an exploded view of the cross section of the wound dressing of FIG. 5.
Figure 6:
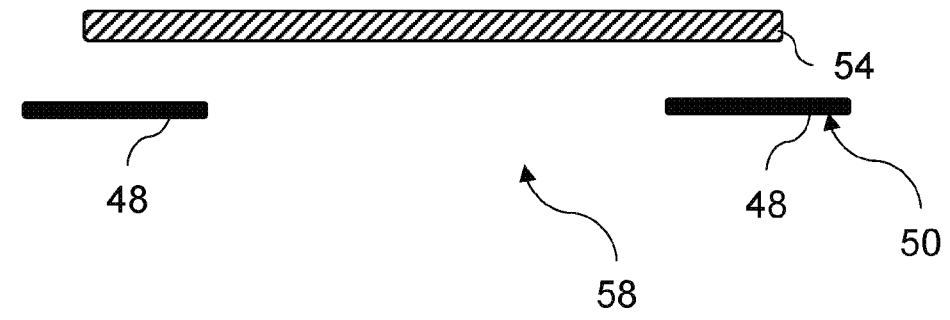
Figure 7:
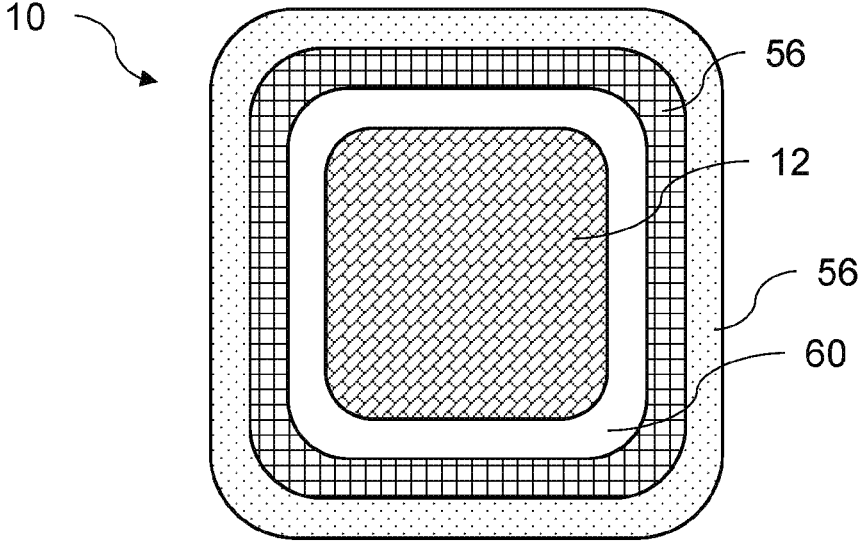
FIG. 7 shows a schematic top view of the wound dressing of FIG. 5.

FIGS. 5, 6 and 7 schematically show a cross section (FIG. 5), an exploded cross section (FIG. 6) and a top view (FIG. 7) of a wound dressing 10 according to the present invention, including the absorbent core 12 shown in FIG. 1. The wound dressing 10 includes a covering layer 46 (also termed backing layer) that adheres to the border region 56' of a proximal wound-contact layer 48. The wound-contact layer 48 has an adhesive layer 50, preferably including a silicone adhesive, on its proximal side that allows the wound dress-ing 10 to adhere to a patient's skin. The wound-contact layer 48 has an opening 58 in its middle to facilitate efficient uptake of the wound exudate.

Between the wound-contact layer 48 and the covering layer 46, the wound dressing encloses a sheath formed by a distal sheath layer 52 and a proximal sheath layer 54 which adhere to each other in their border regions 56. Within the sheath thus formed an absorbent core 12 according to the invention is placed. As the absorbent core 12 is—in its dry state—considerably smaller than the inner space of the sheath, the absorbent core 12 can expand when it takes up wound exudate. The space between the absorbent core 12 in its dry state and the inner side of the sheath is, therefore, termed expansion space 60. The expansion space 60 is sufficiently big to accommodate the expanded superabsor-bent particles 14, 28, 32 after absorbance of wound exudate.

REFERENCE SIGNS LIST 10 wound dressing
12 absorbent core
13 first group
14 superabsorbent particle
16 first water-soluble material
18 microcapsule
20 core
22 shell
24 carrier material
26 second group
28 superabsorbent particle
30 third group
32 superabsorbent particle 34 second water-soluble material
36 proximal surface
38 distal surface
40 proximal layer
42 distal layer
44 channel
46 covering layer
48 wound-contact layer
50 adhesive layer
52 distal sheath layer
54 proximal sheath layer
56,56' border region
58 opening
60 expansion space

The invention claimed is:

1. A wound dressing comprising an absorbent core, the absorbent core comprising: a first group of superabsorbent particles, wherein the superabsorbent particles of the first group are encapsulated in a first water-soluble material, the absorbent core comprises a proximal layer and a distal layer and the first group of superabsorbent particles is comprised in the proximal layer, and wherein the distal layer is free of encapsulated superabsorbent particles.

2. The wound dressing according to claim 1, wherein the absorbent core comprises microcapsules having a core and a shell, wherein the core comprises a superabsorbent particle of the first group and the shell comprises the first water-soluble material.

3. The wound dressing according to claim 2, wherein the concentration of the microcapsules in the most proximal 10 vol.-% of the absorbent core is from 0.1 to 1500 $g/m^2$.

4. The wound dressing according to claim 2, wherein the concentration of microcapsules in the proximal layer is from 0.1 to 17.0 $g/m^2$.

5. The wound dressing according to claim 1, wherein the absorbent core comprises a layer of the first water-soluble material in which the first group of superabsorbent particles is embedded.

6. The wound dressing according to claim 1, wherein the first water-soluble material is selected from the group con-sisting of polyvinyl alcohol, polyvinylpyrrolidones, poly-oxazolines, starch and starch derivatives, polyureas, poly-urethanes, polyethers, polyamides, polyesters, polycarbonates, protein, modified polysaccharides, hydroxyalkyl celluloses, nonionic surfactants with a poly-ethylene residue, salts, and water-soluble combinations and water-soluble derivatives thereof.

7. The wound dressing according to claim 1, wherein the distal layer comprises a carrier material selected from the group consisting of polyester, cellulose, polyurethan, poly-ethylene, polypropylene and combinations and derivatives thereof.

8. The wound dressing according to claim 1, wherein the distal layer comprises a carrier material selected from the group consisting of non-woven, woven, warp-knitted, and weft-knitted material.

9. The wound dressing according to claim 1, wherein the absorbent core comprises a second group of superabsorbent particles which are not encapsulated by a water-soluble material.

10. The wound dressing according to claim 9, wherein the second group of superabsorbent particles form a substan-tially continuous positive concentration gradient through at least a portion of a thickness of the absorbent core between the proximal surface and the distal surface.

11. The wound dressing according to claim 9, wherein the distal layer comprises a carrier material and the second group of superabsorbent particles are distributed in the carrier material.

12. The wound dressing according to claim 1, wherein the absorbent core has a proximal surface and a distal surface and the majority of the superabsorbent particles of the first group are closer to the proximal surface than to the distal surface.

13. The wound dressing according to claim 12, wherein from 55% by weight to 100% by weight of the superabsorbent particles of the first group are closer to the proximal surface than to the distal surface.

14. The wound dressing according to claim 1, wherein the superabsorbent particles of the first group form a substantially continuous negative concentration gradient through at least a portion of a thickness of the absorbent core between the proximal surface and the distal surface.

15. The wound dressing according to claim 1, wherein the proximal layer comprises channels.

16. The wound dressing according to claim 1, wherein the proximal layer comprises a polyester-based carrier material.

17. The wound dressing according to claim 1, wherein the distal layer comprises a cellulose-based carrier material.

18. The wound dressing according to claim 1, wherein the distal layer is adjacent to the proximal layer.

19. The wound dressing according to claim 1 comprising or consisting of
(a) a covering layer;

(b) the absorbent core on a wound-facing side of the covering layer, and
(c) a wound-contact layer on a wound-facing side of the absorbent core.

20. An absorbent core for a wound dressing, wherein the absorbent core comprises a first group of superabsorbent particles which are encapsulated in a first water-soluble material, the absorbent core comprises a proximal layer and a distal layer and the first group of superabsorbent particles is comprised in the proximal layer, and wherein the distal layer is free of encapsulated superabsorbent particles.

21. The absorbent core according to claim 20, wherein the distal layer comprises a carrier material.

22. The absorbent core according to claim 21, wherein:
the proximal layer comprises a carrier material; and
the carrier material of the distal layer has a higher absorption capacity than an absorption capacity of the carrier material of the proximal layer.

23. The absorbent core according to claim 21, wherein:
the proximal layer comprises a carrier material; and
the carrier material of the proximal layer has better wicking properties than the carrier material of the distal layer.

24. The absorbent core according to claim 21, wherein the proximal layer comprises a polyester-based carrier material and the distal layer comprises a cellulose-based carrier material.

*    *    *    *    *